(12) United States Patent
Greenhalgh et al.

(10) Patent No.: US 9,782,107 B1
(45) Date of Patent: Oct. 10, 2017

(54) CENTERING CURSOR

(71) Applicant: Fonar Corporation, Melville, NY (US)

(72) Inventors: John F. Greenhalgh, Greenlawn, NY (US); Mark Gelbien, Levittown, NY (US); Robert Wolf, Medford, NJ (US); Michael Boitano, Smithtown, NY (US)

(73) Assignee: Fonar Corporation, Melville, NY (US)

( * ) Notice: Subject to any disclaimer, the term of this patent is extended or adjusted under 35 U.S.C. 154(b) by 67 days.

(21) Appl. No.: 13/692,627

(22) Filed: Dec. 3, 2012

Related U.S. Application Data

(60) Provisional application No. 61/566,291, filed on Dec. 2, 2011.

(51) Int. Cl.
*A61B 5/00* (2006.01)
*A61B 5/055* (2006.01)

(52) U.S. Cl.
CPC ................... *A61B 5/0555* (2013.01)

(58) Field of Classification Search
CPC ....................................................... A61B 6/04
USPC ........................................................ 600/415
See application file for complete search history.

(56) References Cited

U.S. PATENT DOCUMENTS

| 6,414,490 | B1 | 7/2002 | Damadian et al. |
| 6,677,753 | B1 | 1/2004 | Danby et al. |
| 7,034,535 | B2 * | 4/2006 | Yamagata ..................... 324/318 |
| 7,327,863 | B1 * | 2/2008 | Green et al. .................. 382/128 |
| 2005/0281374 | A1 * | 12/2005 | Cheng et al. .................... 378/68 |
| 2005/0285595 | A1 * | 12/2005 | Green ................ G01R 33/3806 324/307 |

* cited by examiner

*Primary Examiner* — Katherine Fernandez
*Assistant Examiner* — Marjan Saboktakin
(74) *Attorney, Agent, or Firm* — Lerner, David, Littenberg, Krumholz & Mentlik, LLP (57) ABSTRACT

Aspects of the disclosure relate generally to aligning a patient with a target position of a magnetic resonance imaging system. For example, a computer may receive an input identifying a set of coordinates to be aligned with a target position of the magnetic resonance imaging system. The coordinates may correspond to a position of an anatomical feature of a patient within the magnetic resonance imaging system. The computer may also calculate a first travel distance and a second travel distance. Each of the first and second travel distances may be a distance along first and second axes, respectively, along which a patient handling system of the magnetic resonance imaging system is capable of moving. The computer may further reposition the patient handling system according to both the first travel distance and the second travel distance such that the anatomical feature is aligned with the target position.

22 Claims, 9 Drawing Sheets

CENTERING CURSOR

CROSS-REFERENCE TO RELATED APPLICATIONS

The present application claims the benefit of the filing date of U.S. Provisional Patent Application No. 61/566,291 filed Dec. 2, 2011, the disclosure of which is hereby incorporated herein by reference.

BACKGROUND

This disclosure is directed to a system and method for centering the scan region of an object in the isocenter of a magnetic resonance imaging magnet. Magnetic resonance imaging ("MRI") offers numerous advantages over other imaging techniques. MRI does not expose either the patient or medical personnel to X-rays and offers important safety advantages. Also, MRI can obtain images of soft tissues within the body which are not readily visualized using other imaging techniques. In MRI, an object to be imaged as, for example, a body of a human subject is exposed to a strong, substantially constant static magnetic field. The static magnetic field causes the spin vectors of certain atomic nuclei within the body to randomly rotate or "precess" around an axis parallel to the direction of the static magnetic field. Radio frequency excitation energy is applied to the body, and this energy causes the nuclei to "precess" in phase and in an excited state. As the precessing atomic nuclei relax, weak radio frequency signals are emitted; such radio frequency signals are referred to herein as magnetic resonance signals.

Different tissues produce different signal characteristics. Tissues having a high density of nuclei will produce stronger signals than tissues with a low density of such nuclei. Furthermore, relatively small gradients in the magnetic field are superimposed on the static magnetic field at various times during the process, so that magnetic resonance signals from different portions of the patient's body differ in phase and/or frequency. If the process is repeated numerous times using different combinations of gradients, the signals from the various repetitions together provide enough information to form a map of signal characteristics versus location within the body. Such a map can be reconstructed by conventional techniques well known in the MRI art, and can be displayed as a pictorial image of the tissues as known in the art.

In MRI, it is important that the object that's being imaged, e.g., predetermined portion of a patient's anatomy, be located at the isocenter of the magnet. This positioning advantageously allows the images of the anatomy of interest to be in, what is colloquially referred to as, the sweet spot of the magnet. This allows for better and higher contrast images.

Conventionally, MRI machines require that a patient lie in a horizontal position and then be advanced into a tubular enclosure within a super-conducting solenoidal magnet used to generate the static magnetic field. Ferromagnetic frame magnets having horizontal pole axes have been developed, which allow a patient to be imaged in a variety of positions including, for example, upright (sitting or standing), recumbent, Trendelenburg and reverse-Trendelenburg positions.

More specifically, ferromagnetic frame magnets having horizontal pole axes have been disclosed, for example, in commonly assigned U.S. Pat. No. 6,414,490, the disclosures of which are incorporated by reference herein, and U.S. Pat. No. 6,677,753, filed on Nov. 22, 2000, the disclosure of which is also incorporated by reference herein. A magnet having poles spaced apart from one another along a horizontal axis provides a horizontally oriented magnetic field within a patient-receiving gap between the poles. Such a magnet can be used with a patient positioning device including elevation and tilt mechanisms to provide extraordinary versatility in patient positioning. For example, where the patient positioning device includes a bed or similar device for supporting the patient in a supine or recumbent position, the bed can be tilted and/or elevated so as to image the patient in essentially any position between a fully standing position and a fully supine or fully recumbent position, and can be elevated or lowered so that essentially any portion of the patient's anatomy is disposed within the gap in an optimum position for imaging. As further disclosed in the aforesaid patents, the patient positioning device may include additional elements such as a platform, any type of seat, or both, projecting from the bed to support the patient when the bed is tilted towards a standing orientation. Still, other patient supporting devices can be used in place of a bed in a system of this type. Thus, magnets of this type provide extraordinary versatility in imaging.

For example, these systems allow evaluation of the spine in all of its weight bearing (e.g., neutral, flexion and extension) and recumbent positions. In order to enable proper diagnosis of back pain, for example, it is usually important that a particular area of anatomical interest (e.g., a particular vertebrae) be evaluated in these different positions.

However, in switching from one of these positions to another, the patient is intentionally repositioned in a new position, resulting in a fairly large movement of the anatomy of interest both relative to neighboring anatomy, and relative to the imaging region in the magnet. Furthermore, repositioning a patient from one of the upright positions to the recumbent position, and vice versa, may involve removal of the patient from the imaging volume, and either removal or addition of a seat to the patient positioning bed before repositioning the patient in the imaging volume. Here, the change in the position of the patient's anatomy is rather extreme. These examples illustrate the need to have a method and system, that would improve alignment of the isocenter of the magnet with the anatomy of interest.

BRIEF SUMMARY OF THE INVENTION

One aspect of the disclosure provides for a method of aligning a patient with a target position of a magnetic resonance imaging system. The method may include receiving, at a computer, an input identifying a set of at least two coordinates to be repositioned in alignment with the target position. The at least two coordinates may correspond to a position of an anatomical feature within the magnetic resonance imaging system. The method may also include calculating, at the computer, a first travel distance and a second travel distance, wherein each of the first and second travel distances is a distance along first and second axes, respectively, along which the magnetic resonance imaging system is capable of translating or reorienting in order to reposition the patient. The method further includes repositioning the patient within the magnetic resonance imaging system according to both the first travel distance and the second travel distance.

In some aspects of the disclosure, the first axis may correspond to a degree of freedom of the magnetic resonance imaging system along which a carriage supporting the patient is capable of moving. In some aspects, the second axis may correspond to a degree of freedom of the magnetic resonance imaging system along which a patient support supporting the patient is capable of moving.

In some aspects of the disclosure the method may further include displaying a two-dimensional representation of the patient, wherein each point of the displayed two-dimensional representation corresponds to a position within the magnetic resonance imaging system.

In some aspects of the disclosure, the method may yet further include calculating first and second maximum ranges along each of the first and second axes, respectively, comparing the first maximum range to the first travel distance, and comparing the second maximum range to the second travel distance. If neither of the travel distances exceeds the corresponding maximum range, the method may include repositioning the patient within the magnetic resonance imaging system according to both the first travel distance and the second travel distance. If either of the travel distances exceeds the corresponding maximum range, the method may include providing a signal to the user indicating an out-of-range error. The out-of-range error may also include an indication as to which of the first travel distance and the second travel distance exceeds the corresponding maximum range.

In some aspects of the disclosure, the target position may be the isocenter of the magnetic resonance imaging system. In one aspect, the isocenter may include any point within a 0.1 mm radius of a centerpoint of a magnet included in the magnetic resonance imaging system. In another aspect, the isocenter may include any point within a 1.0 mm radius of a centerpoint of a magnet included in the magnetic resonance imaging system. In yet another aspect, the isocenter may include any point within a 2.0 cm radius of a centerpoint of a magnet included in the magnetic resonance imaging system.

Another aspect of the disclosure provides for a device including memory storing information pertaining to a current position of a patient handling system within a magnetic resonance imaging system, and a processor coupled to the memory. The processor may be configured to receive an input identifying a set of at least two coordinates to be repositioned in alignment with an isocenter of the magnetic resonance imaging system. The at least two coordinates may correspond to a position of a target anatomical feature of a patient within the magnetic resonance imaging system. The processor may also be configured to calculate a first travel distance and a second travel distance. Each of the first and second travel distances may be a distance along first and second axes, respectively, along which the patient handling system is capable of translating or reorienting. The processor may further be configured to reposition the patient handling system, according to both the first travel distance and the second travel distance, from the current position to the isocenter.

In some aspects, the first axis may correspond to a degree of freedom along which a component of the patient handling system is capable of translating parallel to one of an anterior, superior, or left axis of the patient. In another aspect, the first axis may correspond to a degree of freedom along which a component of the patient handling system is capable of linearly moving relative to at least one rail. In yet another aspect, the second axis may correspond to a degree of freedom along which a component of the patient handling system is capable of linearly moving relative to at least one slab. The first axis and the second axis may be nonorthogonal.

In some aspects of the disclosure, the processor may be further configured to display image data. The image data may include a two-dimensional representation of the patient, wherein each point of the displayed two-dimensional representation may correspond to a position within the magnetic resonance imaging system.

In some aspects of the disclosure, the processor may be further configured to receive information indicating the current position of a patient handling system from a first file, receive information indicating the current position of a patient handling system from a second file, the second file including the image data displayed by the processor, and compare the received information of the first file to the received information of the second file. If the received information of the first file substantially corresponds to the received information of the second file, the processor may reposition the patient within the magnetic resonance imaging system according to both the first travel distance and the second travel distance.

DETAILED DESCRIPTION

One object of the present invention is to provide a device that allows for automatic centering of the anatomy of interest as a patient or the patient support changes position. The device serves to improve the quality of imaging yielded by magnetic resonance imaging ("MRI"). This and other objectives are realized by use of a processor-based machine that is programmed to acquire a user selected target anatomical feature of a patient and control the positioning of a bed on which the patient is located such that the target anatomical feature is aligned with a target position in a magnetic resonance imaging system ("MRI system"), such as the isocenter of the MRI magnet.

Yet another object of the present disclosure is to provide a method of automatically centering the anatomy of interest as a patient or the patient support changes position.

Another object of the present disclosure is to provide a system in which a targeted anatomical feature may be automatically centered as the patient or the patient support changes position. The system may comprise a magnetic resonance imaging magnet and computer or processor based apparatus that controls a patient bed associated with the magnet. The processor based apparatus may operate under the control of instructions that cause the bed to automatically realign the anatomy of interest with the target position if the bed is rotated, translated or its position is otherwise adjusted. In addition, the system may include an upright magnetic resonance imaging magnetic apparatus such as those offered for sale by Fonar Corporation. Nonetheless, the invention is equally applicable in a more conventional recumbent scanner.

Figure 1:
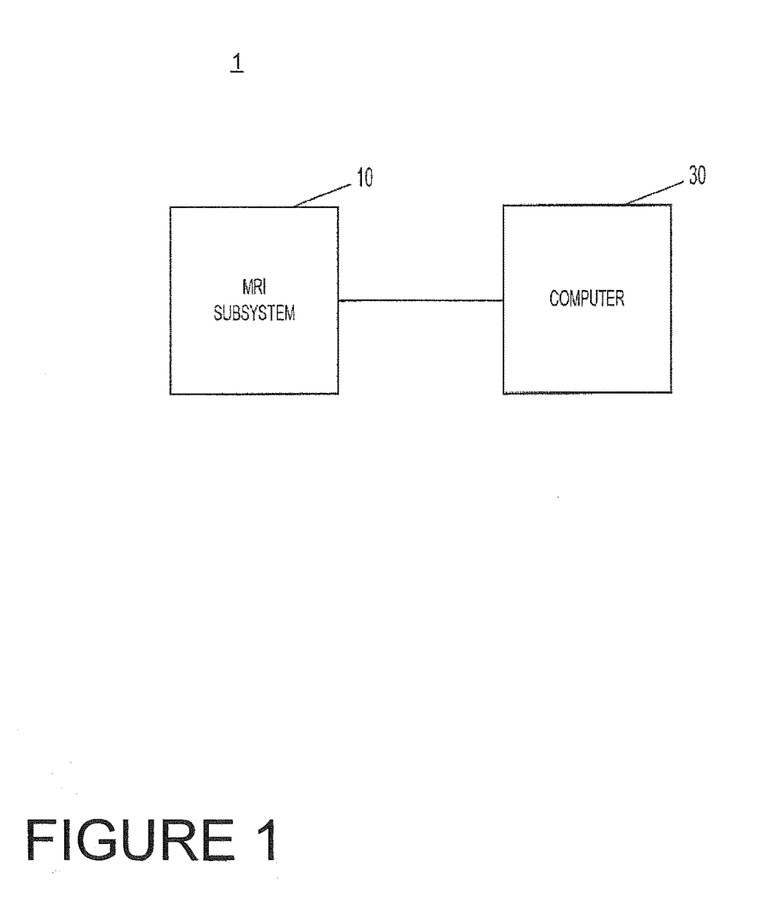
FIG. 1 illustratively depicts a system in accordance with aspects of the disclosure.

FIG. 1 illustratively depicts an MRI system in accordance with an aspect of the present invention. Turning now to FIG. 1, the system 1 includes an MRI subsystem 10 and computer 30. The MRI subsystem 10 operates under the control of computer 30. The subsystem 10 and computer 30 may be connected over a network or via a direct connection. The networks may include a local area network running Ethernet or other network protocols, WiFi or any other type of network that enables communications between two devices. The computer is operable to control the subsystem 10 in acquiring images, including pulse sequence generation, image acquisition and reconstruction.

In general, the subsystem preferably allows patient to be imaged in positions other than just the recumbent position. For example, FIG. 2 of the current application shows a sectional view of an MRI magnet subsystem 100 that can be used in accordance with a preferred embodiment of the present application. MRI magnet subsystem 100 includes a magnet having a ferromagnetic frame 102, a flux generating means 104 as is described in further detail below, and a patient handling system 106. The ferromagnetic frame 102 includes a first side wall 108 and a second side wall (not shown). The side walls extend vertically. For purposes of clarity, FIG. 2 does not show the second side wall or any of its associated structures (though it should be understood that the second side wall will include elements similar to those contained in the first side wall 108). The ferromagnetic frame 102 also includes a top flux return structure 112 and a bottom flux return structure 114. The top flux return structure 112 may include two columns 116 and 118. Between these two columns, a top opening 120 is defined. Similarly, the bottom flux return structure 114 may include two columns 122 and 124 that together define a bottom opening 126. Thus, the side walls and the flux return members 112 and 114 form a rectilinear structure, with the top flux return structure 112 constituting the top wall of the rectilinear structure, the bottom flux return structure 114 constituting the bottom wall of the rectilinear structure and the side walls forming the side walls of the rectilinear structure. The frame 102 of the rectilinear structure defines a front patient opening 128 on one side of the frame 102 and a similar back patient opening 130 on the opposite side of the frame 102. The ferromagnetic frame 102 further includes a first magnetic pole 132 and a second magnetic pole (not shown, but horizontally displaced opposite the first magnetic pole 132). The first magnetic pole 132 extends from the first side wall 108 towards the second side wall and the second magnetic pole extends from the second side wall towards the first side wall 108. The magnetic poles are generally cylindrical and are coaxial with one another on a common horizontal polar axis (in the direction extending out of the page of the figure). Between the magnetic poles is a gap 131, also referred to as the patient-receiving space, of the magnet. The gap or patient-receiving space 131 is accessed by the front patient opening 128, the back patient opening 130, the top opening 120 or the bottom opening 126.

Figure 2:
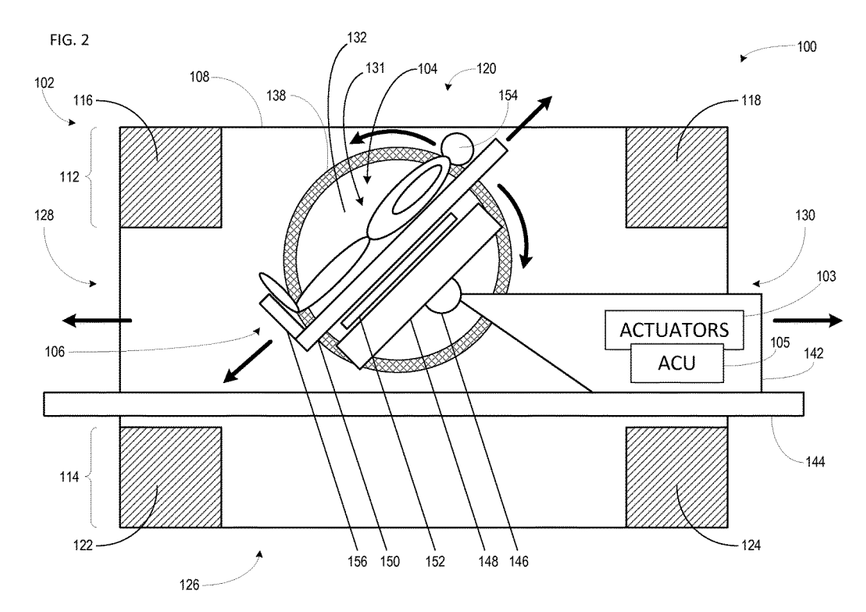
FIG. 2 illustratively depicts an MRI magnet subsystem in accordance with aspects of the disclosure.

The flux generating means 104 includes a first electromagnetic coil assembly 138 which surrounds the first magnetic pole 132, and a second electromagnet coil assembly, which surrounds the second magnetic pole (not shown but comparable to the first electromagnetic coil assembly 138). These electromagnetic coil assemblies 138 and 140 may be either resistive or superconductive.

The patient handling system 106 may be capable of several degrees or axes of motion. The patient handling system 106 may be termed a stand-up patient handling system, although the patient handling system 106 is not limited to standing position applications. The patient handling system 106 may include a carriage 142 mounted on rails 144. The carriage 142 may move linearly back and forth along the rails 144. The rails 144 typically do not block the bottom open space 126.

A generally horizontal pivot axis 146 may be mounted on carriage 142. An elevator frame 148 may be mounted to the pivot axis 146. The carriage 142 may be operable to rotate the elevator frame 148 about the pivot axis 146. A patient support 150 may be mounted on the elevator frame 148. The patient support 150 may be moved linearly along the elevator frame 148 by an actuator 152.

In some examples of the disclosure, the patient handling system 106 may further include an actuator capable of moving either the carriage 142 or the patient support 150 along the patient's left axis (in the example of FIG. 2, moving in and out of the page). In some examples, the patient handling system 106 may include an actuator capable of raising or lowering either the carriage 142 or the patient support 150 (in the example of FIG. 2, perpendicular to the motion of the patient support 150 along the elevator frame 148). Thus, a patient 154 may be positioned with several degrees of freedom, or along several axes of movement or motion. Specifically, the patient handling system 106 may be capable of moving a patient 154 in any of the four linear directions described above, and may rotate the patient 154 around at least the one rotational axis described above. In the example of FIG. 2, the solid black arrows demonstrate three of the several axes of movement possible with the patient handling system 106, particularly the linear back-and-forth movement of the carriage along the rails, the rotational movement of the elevator frame 148 about the pivot axis 146, and the linear movement of the patient support 150 along the elevator frame 148. In some examples, such as the example of FIG. 2, the rails 144 may be mounted such that portions of patient 154 may be positioned below the rails 144 through a bottom open space 126.

Often, a foot rest 156 may be used in order to support a patient in a standing position. Given the wide variety of positions possible with the patient handling system 108, many other such supports may be implemented, such as chair seats or straps.

The patient handling system 106 incorporates one or more actuators 103 and an actuation control unit 105. Actuators 103 may be conventional electrical, electromechanical, pneumatic, hydraulic or other devices capable of imparting the desired motion to the elements of the patient handling system. For example, the actuators may include elements such as conventional stepper motors or other conventional electric motors linked to the elements of the patient handling system 106. The actuator control unit 105 may incorporate a conventional programmable controller, microprocessor, or computer with appropriate input and output interfaces. The actuation control unit 105 is linked to a control computer (such as computer 30) and to the manual controls which regulate the patient handling system. The actuation control unit may be mounted in proximity to the actuators 103 as, for example, on carriage 142.

Figure 3:
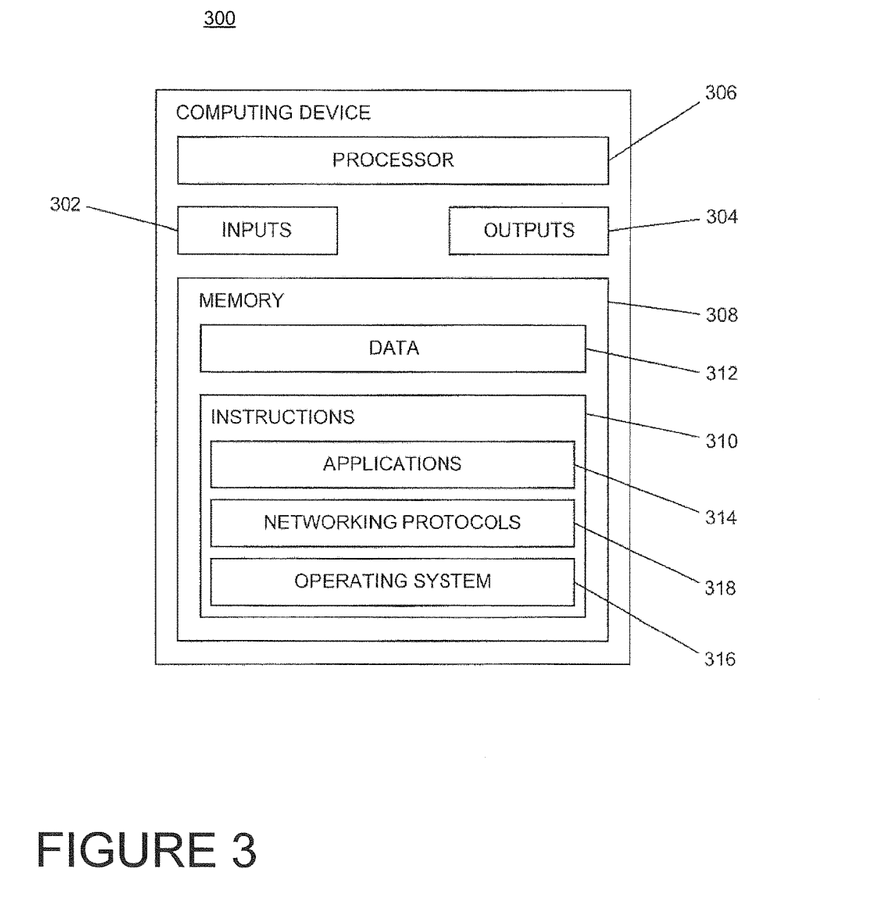
FIG. 3 is a computer apparatus in accordance with an aspect of the disclosure.

FIG. 3 shows an apparatus 300 for implementing the computer 30 depicted in the system 1 presented in FIG. 1. As seen therein, apparatus 300 illustrates one configuration of a computing device that may be used to control the MRI subsystem in accordance with method steps described below.

The apparatus 300 may include, for example, one or more user inputs 302 such as a keyboard and mouse and/or other types of input devices such as pen-inputs, joysticks, buttons, touch screens, etc., as well as a display 304, which could include, for instance, a CRT, LCD, plasma screen monitor, TV, projector, etc. As shown, apparatus 300 further contains a processor 306, and memory or computer readable medium 308.

Memory 308 stores information accessible by processor 306, including instructions 310 that may be executed by the processor 306 and data 312 that may be retrieved, manipulated or stored by the processor. The memory 308 may be of any type capable of storing information accessible by the processor, such as a hard-drive, ROM, RAM, CD-ROM, DVD, Blu-Ray disk, flash memories, write-capable or read-only memories. The processor 306 may comprise any number of well known processors, such as processors from Intel Corporation and Advanced Micro Devices. Alternatively, the processor 306 may be a dedicated controller for executing operations, such as an ASIC.

The instructions 310 may comprise any set of instructions to be executed directly (such as machine code) or indirectly (such as scripts) by the processor. In that regard, the terms "instructions," "applications" and "programs" are used interchangeably herein. The instructions may be stored in any computer language or format, such as in executable/object code or modules of source code.

Data 312 may be retrieved, stored or modified by processor 306 in accordance with the instructions 310. The data may be stored as a collection of data. For instance, although the invention is not limited by any particular data structure, the data may be stored in computer registers, in a relational database as a table having a plurality of different fields and records, XML documents, or flat files.

The data may also be formatted in any computer readable format such as, but not limited to, binary values, ASCII etc. Similarly, the data may include images stored in a variety of formats. Moreover, the data may include any information sufficient to identify the relevant information, such as descriptive text, proprietary codes, pointers, references to data stored in other memories (including other locations in a network) or information which is used by a function to calculate the relevant data.

Data 312 may include patient identification information. The patient identification information may be useful for properly identifying an image that is displayed on the display 304 as an image of a particular patient, and may further be useful for verifying that the correct image is displayed.

Data 312 may also include information pertaining to the current position and orientation of the patient handling system 106 within the MRI magnet subsystem 100. As described above, the patient handling system 106 is capable of moving along three degrees of freedom, specifically along two linear axes and a third rotational axis. In some examples, the current position and orientation of the patient handling system 106 may be represented in the data 312 in terms of these three axes. In other examples, the current position and orientation of the patient handling system 106 may be represented in the data 312 in terms of a different set of axes, such as in terms of an anterior, a sagittal, and a left axis. It will be understood by those of ordinary skill in the art that the position and orientation of an object in three-dimensional space may be represented in terms of several sets of axes, and that any of such sets of axes may be used to represent such information in the data 312.

In further examples, the position of the carriage 142 may be represented in terms of its relative position on the rails 144 and the position of the patient support 150 on the elevator frame 148. Such information may be beneficial for determining how much further the carriage 142 and/or patient support 150 may be moved within the patient handling system 106.

Data 312 may further include information pertaining to a user input. For example, the data may include information regarding a current position of a user-controlled cursor appearing on the display 304. The position of such a user-controlled cursor may be represented in the data 312 in terms of an x-coordinate and a y-coordinate corresponding to coordinates of the display screen. The position may further be represented in the data 312 in terms of a three dimensional space, such as the axes described above, such that each point of the display is associated with a coordinate of the MRI magnet subsystem 100. In some aspects of the disclosure, such data may also be displayed to a user, for instance via the display 304.

Although the processor 306 and memory 308 are functionally illustrated in FIG. 3 as being within the same block, it will be understood that the processor and memory may actually comprise multiple processors and memories that may or may not be stored within the same physical housing or location. For example, some or all of the instructions and data may be stored on a computer-readable removable recording medium such as a CD-ROM, DVD or Blu-Ray disk. Alternatively, such information may be stored within a read-only computer chip. Some or all of the instructions and data may be stored in a location physically remote from, yet still accessible by, the processor. Similarly, the processor may actually comprise a collection of processors which may or may not operate in parallel. Data may be distributed and stored across multiple memories 308 such as hard drives, data centers, server farms or the like.

In addition, the memory 308 in apparatus 300 may include one or more applications or programs 314 adapted to provide any of the functions described with respect to the computer 30 and in accordance with the various aspects of the invention discussed above and below. Each device may include and execute specific instructions or applications, desirably under management of the processor 306 in conjunction with an operating system 316 and networking protocols instructions 318 to provide the functionality described above.

Operations in accordance with aspects of the disclosure will now be described with reference to the figures. It should be understood that the following operations do not have to be performed in the precise order described below. Rather, various operations can be handled in a different order or simultaneously. It should also be understood that these operations do not have to be performed all at once. For instance, some operations may be performed separately from other operations.

Figure 4:
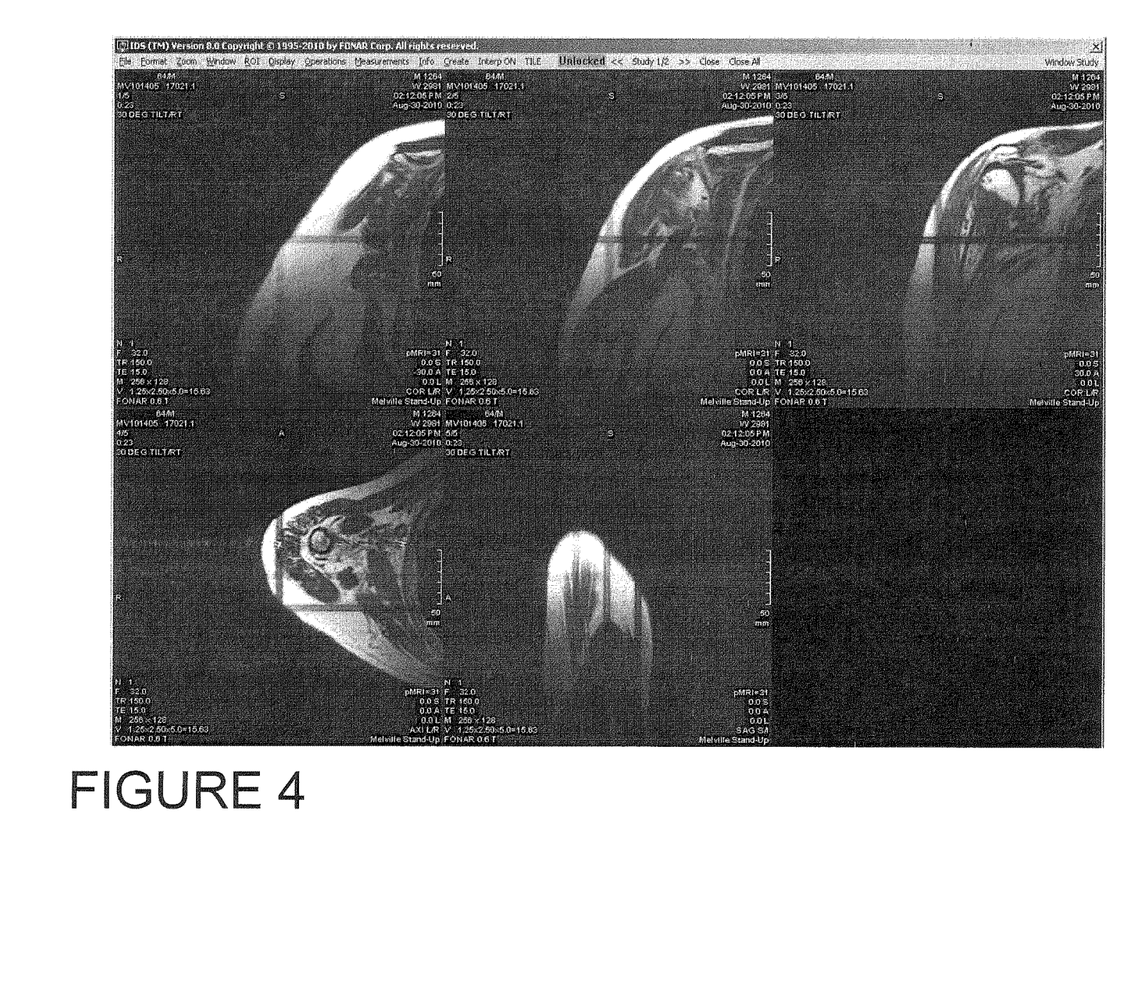
FIGS. 4-6 are example images displayed by the apparatus of FIG. 3 in accordance with an aspect of the disclosure.

The apparatus 300 may display one or more cross-sectional images of a patient 154 positioned in the MRI magnet subsystem 100. An example image is depicted in FIG. 4. In the example of FIG. 4, the apparatus 300 displays five cross-sectional images of a shoulder of a patient who is in a lateral decubitus position. Each of the top three images is a slice of a multi-planar cross-section of the patient's shoulder taken along a coronal plane of the patient. The bottom two pictures are cross-sectional images of the patient's shoulder taken along an axial plane and a sagittal plane of the patient, respectively. The head of the humerus is visible most clearly in the upper right image, a planar cross-sectional image taken along the coronal plane with an anterior shift of 30 mm.

The image or images displayed by the apparatus may be generated and updated regularly. In some examples of the disclosure, regular updating may include updating the image upon movement of the patient handling system 106. In other examples, regular updating may occur automatically, for example after every couple of minutes or seconds, or even in realtime. One advantage of automatically updating the displayed images is that such updating may inform a user of the MRI system 100 when the patient 154 inadvertently moves out of the patient's original position.

In addition to displaying the cross-sectional images, the apparatus may also display information about the displayed image, the patient, and a user input.

Information about the displayed image may include a current bed angle position. In the example of FIG. 4, the image indicates a bed angle of 31° ("pMRI=31" displayed on bottom right corner of each image). Each image may also indicate the time and date that the image was taken, and further provide a corresponding slice number. In the example of FIG. 4, each image indicates in an upper left corner a time and date of 2:12:05 PM and Aug-30-2010 of the image and a slice number ("1/5," "2/5," etc.).

In some examples of the disclosure, at least one of the images may indicate the position of a target position in the MRI magnet subsystem 100. The target position may be located at the centerpoint of the image, or may be offset from the centerpoint. The target position may refer to any position in the MRI magnet subsystem 100 with which it is desirable to align an anatomical feature of the patient 154. Often, the target position of the MRI magnet system 100 is the isocenter of the system. The isocenter may refer to the centerpoint of the magnet in the MRI magnet subsystem, whether such magnet is an Upright®, a Quad 12000, or a 3.0 T superconducting magnet. In some contexts, the isocenter may better be thought of as a point directly in between and equidistant from each of the first magnetic pole 132 and the second magnetic pole 134. The identification of the isocenter may be important because the magnetic field ($B_0$) and the transmitted RF field ($B_1$) are most uniform at this point and the gradient magnetic fields are most pure and linear. Therefore, by centering the images at the isocenter, uniformity and clarity of the images may be improved. In the example of FIG. 4, the isocenter is located at the center of the upper middle image (slice 2/5). In other examples, as noted above, the isocenter may be offset from the center of some or all displayed images in other examples of the disclosure, or may not appear in any of the images.

For purposes of this disclosure, the term "target position" may be understood to include more than a single infinitesimal point. Rather, the target position may include any point within a certain distance from the point with which it is desirable to align an anatomical feature of the patient 154.

For example, the carriage 142 and patient support 150 may only move linearly in discrete increments of about 0.1 millimeters, increments of about 1 millimeter, or increments of about 2 centimeters. As such, the patient handling system 106 may be limited in how precisely it may align a selected anatomical feature with the target position. Accordingly, in the above examples, the target position may include any point within about 0.1 millimeters to about 2 centimeters of the point with which it is desirable to align an anatomical feature of the patient 154, depending on the precision of the respective system's patient handling system 106.

For further example, the image from which an anatomical feature is selected may have poor resolution. A user selecting a portion of the image to align with the target position may not be able to precisely select a desired anatomical feature, due to the poor image resolution. In such an example, the target position may include any point within a resolution of the image (e.g., a distance between pixels of the image, a distance between visually distinguishable portions of the image) from which the anatomical feature is selected.

In some examples, the target position may be understood to refer to a point that is closer to the isocenter than any other point with which the patient handling system is capable of aligning. For instance, in an MRI system that exhibits movement along only two degrees of freedom, it is possible that the anatomy of interest can be positioned directly between the first magnetic pole 132 and the second magnetic pole 134, but cannot necessarily be positioned at a location equidistant from the magnetic poles. In such an instance, it may still be preferable to align the anatomy of interest along the two available degrees of freedom such that the anatomy of interest is between the first magnetic pole 132 and the second magnetic pole 134.

FIG. 4 provides an example in which aligning the anatomy of interest with a target position that is not the isocenter may be preferable. In the example of FIG. 4, each of images 1/5 and 3/5 may include a target position at the center of each image. Although neither the center of image 1/5 nor that of image 3/5 is at isocenter of the MRI magnet subsystem 100, the center of each image is still closer to the isocenter than any other portion of either image. As such, it may be advantageous to reposition an anatomy of interest (e.g., the center the head of the humerus in image 3/5) such that it is closer to the isocenter, even if that anatomy of interest cannot be perfectly aligned with the isocenter.

The apparatus 300 may also display a centering cursor. The centering cursor may be controlled by a user such that the user may interact with the image by overlaying the cursor on top of a portion of the image which the user wishes to select. The centering cursor may be positioned over any portion of any of the images displayed on the display 304, or anywhere else on the screen, such as over a toolbar (e.g., at the top of the screen in the example image of FIG. 4).

In addition, the apparatus 300 may display information regarding the position of the centering cursor. In the example of FIG. 4, each of the cross-sectional images displayed includes a superior coordinate ("S"), an anterior coordinate ("A") and a left coordinate ("L"). In the example of FIG. 4, the coordinates displayed in each image correspond to the coordinates of the center point of each image. Although the cross-sectional images displayed are two-dimensional, each image may be mapped according to a three-dimensional space in which the image constitutes a plane. Additional information, such as spatial inputs (e.g., the current bed angle and the current position and orientation of the patient handling system 106), may be employed in mapping the cross-sectional image according to the three-dimensional space. In the example of FIG. 4, each of the five displayed images is mapped according to a superior, an anterior, and a left axis, such that the midpoint of each axis is positioned at isocenter. As such, superior and left coordinates of the top three images, which are taken along a coronal plane of the patient 154, are identical, whereas the anterior coordinate of each image is different. Specifically, the centerpoint of the upper left image (slice 1/5) is shifted −30 mm posteriorly away from isocenter, and the centerpoint of the upper right image (slice 3/5) is shifted +30 mm anteriorly away from isocenter.

Figure 5:
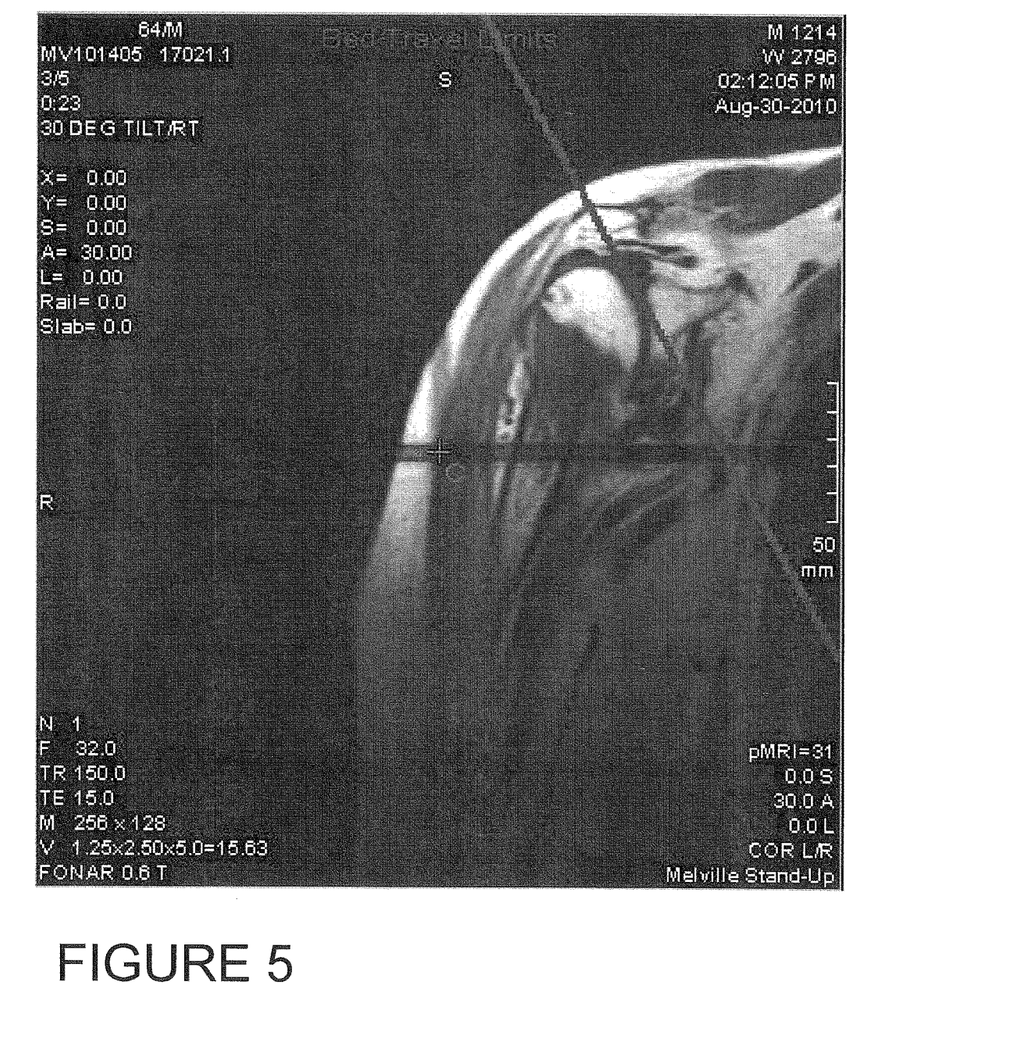

A user may select a point on the image displayed by the apparatus 300. Selection of the point may be performed by dragging a cursor displayed on the display 304 over a portion of the displayed image, such that the cursor overlays that portion. Often, the user overlays the cursor with an anatomical feature of the patient 154 which the user desires to align with the target position (e.g., isocenter). FIG. 5 depicts an example image including a cursor that may be controlled by the user. In the example of FIG. 5, a cursor, represented by crosshairs, appears at the center of the image. In other examples of the disclosure, the cursor may appear at other portions of the image and may be represented by other symbols.

Figure 6:
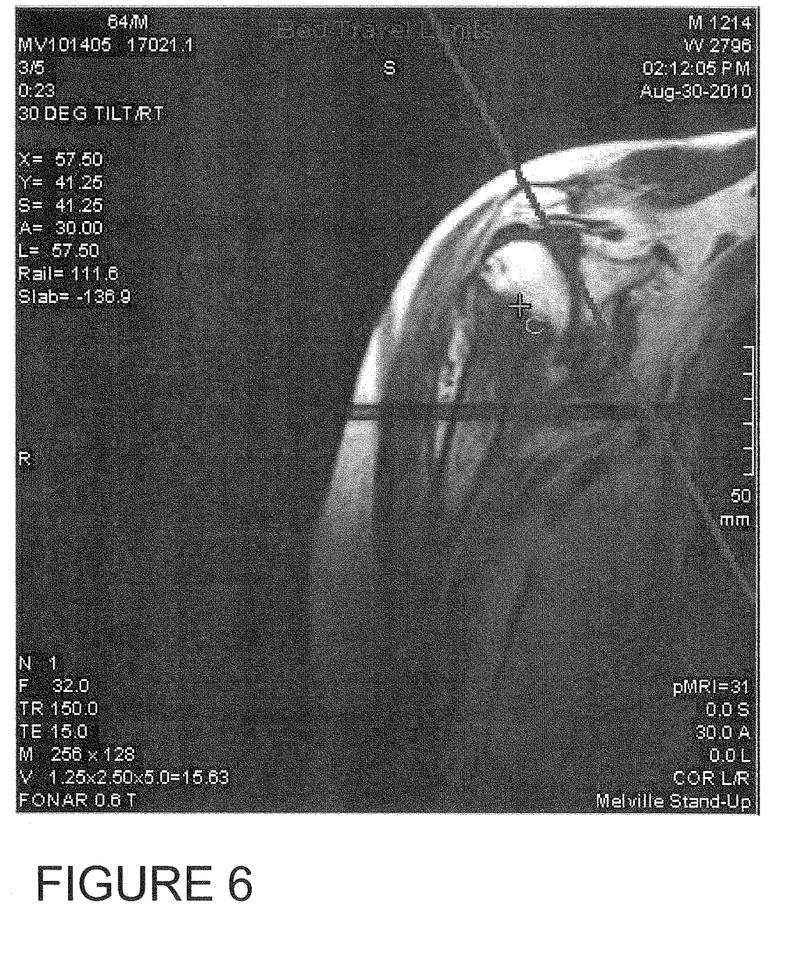

FIG. 6 depicts a user-modified version of the image of FIG. 5 in which the cursor has been moved by the user. In the example of FIG. 6, the cursor is positioned to overlay the head of the patient's humerus. In other examples of the disclosure, the cursor may be positioned to overlay another anatomical feature, depending on the anatomical feature for which is the user desires to improve image clarity.

FIGS. 5 and 6, in addition to depicting the position of the cursor, may also depict information relating to a coordinate at which the cursor is positioned. In the example of FIG. 5, "S" and "L" coordinates are displayed towards the upper left corner of the image. These coordinates indicate that the cursor, while centered in the image, is located at the midpoint of each of the superior/inferior and left/right axes. In the example of FIG. 5, the midpoint of the axes is also the midpoint of the image, though in other examples of the disclosure the midpoint of the axes may correspond to an off-center point of the image. In the example of FIG. 6, the "S" and "L" coordinates are updated to indicate the offset of the cursor from the center of the image. Specifically, the updated "S" coordinate is 41.25, indicating a displacement of about 41.25 mm along the superior axis, and the updated "L" coordinate is 57.50, indicating a displacement of the cursor of about 57.50 mm along the left axis.

In the examples of FIGS. 5 and 6, an "X" coordinate and a "Y" coordinate are also displayed on the display 304 of the apparatus 300. The "X" and "Y" coordinates may correspond to coordinates of the displayed two-dimensional image. In the examples of FIGS. 5 and 6, these coordinates are identical to the superior/inferior and left/right coordinate axes, particularly because the displayed image is taken along the coronal plane. In other examples of the disclosure, the "X" and "Y" coordinates may correspond to other axes such that they are not identical to the superior/inferior and left/right coordinates, depending on the plane along which the image is taken. The apparatus 300 may calculate two or more travel distances between the target position and the portion of the image selected by the user. Each of the travel distances may indicate a distance necessary to move a component of the patient handling system 106 in order to reposition the patient 154 such that the target anatomy of the patient 154 is aligned with the target position of the MRI magnet subsystem 100. The calculation may be performed by a program stored in the computer 30 of system 1, shown in FIG. 1.

Calculation of the travel distances may include a transformation from a first coordinate system to a second coordinate system. For example, the apparatus 300 may identify the space occupied by the anatomy of the patient in terms of a first coordinate system (e.g., a superior/anterior/left coordinate system), and the axes along which the patient handling system is capable of moving and/or rotating in terms of a second coordinate system (e.g., a rail/pivot axis/slab coordinate system). In such an example, the apparatus 300 may map a point in one coordinate system (e.g., a point selected by the user, a target position) to a corresponding point in the other coordinate system. Likewise, the apparatus may map a vector in one coordinate system (e.g., one or more vectors connecting a point selected by the user to a target position, etc.) to a corresponding vector in the other coordinate system. For further example, the apparatus 300 may correspond the distance between a user selected portion of the image and the target position of the image (e.g., one or more vectors in the first coordinate system, to which the image is mapped, as described above) to a movement of the patient handling system 106 along its degrees of freedom (e.g., one or more vectors in the second coordinate system).

For purposes of illustration, in the examples of FIGS. 5 and 6, a "rail" distance and a "slab" distance are each calculated, and these calculated distances are displayed with the image in the display 304. The "rail" distance indicates a distance necessary to move the carriage 142 of the patient handling system 106 along the rails 144 in order to reposition the patient 154 such that the target anatomy of the patient 154 is aligned with the target position of the MRI magnet subsystem 100. The "slab" distance indicates a distance necessary to move the patient support 150 of the patient handling system 106 along the elevator frame 148.

In the examples of FIGS. 5 and 6, the rail and slab distances are calculated by means of a coordinate transformation. Specifically, the apparatus 300 may calculate a coordinate transformation through which points and vectors in the rail and slab coordinate system may be mapped against points and vectors of the superior/anterior/left coordinate system of the image. The calculated transformation may change as the two coordinate systems shift relative to one another. For example, if the patient handling system 106 is rotated about the pivot axis 146, the slab axis may move relative to the rail axis, in turn resulting in an updated rail/slab coordinate system. Accordingly, an updated coordinate transformation may be required to properly map the superior/anterior/left coordinate system against the updated rail/slab coordinate system.

Figure 7:
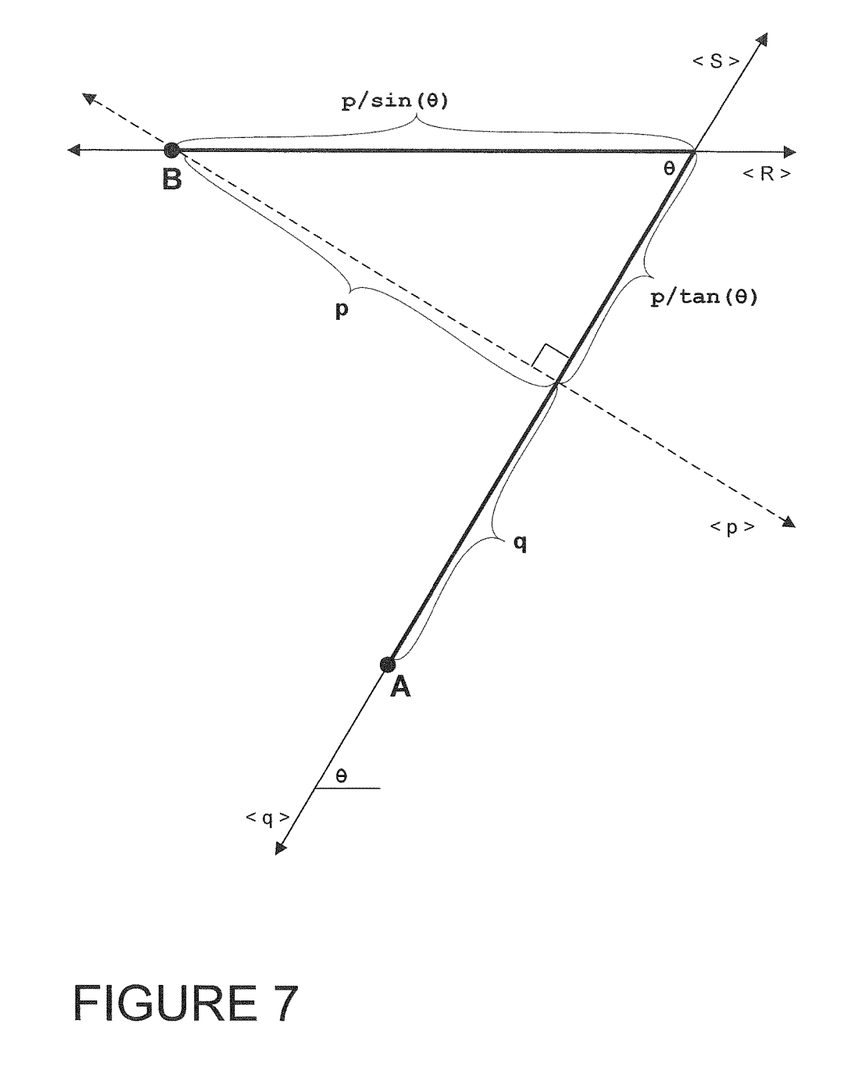
FIG. 7 is a diagram of a coordinate space in accordance with an aspect of the disclosure.

The coordinate transformation applied in FIGS. 5 and 6 is illustrated in the diagram of FIG. 7. In FIG. 7, points A and B (which correspond to the portion of an image selected by a user and the target position, respectively) are mapped along two coordinate systems, each denoted by axis labels <p,q> and <R,S>. The axes of the <p,q> coordinate space are orthogonal to one another. In the example of FIGS. 5 and 6, the p axis corresponds to the X axis and the q axis corresponds to the Y axis. The axes of the <R,S> coordinate space, which correspond to the degrees of freedom of the patient support system 106, are not orthogonal, and the angle between the axes is denoted as θ. In the example of FIGS. 5 and 6, θ equals the bed angle, 31°.

The travel distance between points A and B may then be represented in terms of a sum of vectors p and q, or in terms of a sum of vectors R and S. In the example of FIG. 7, the apparatus 300 may use the previously calculated p and q vectors in the <p,q> coordinate space to calculate the R vector and S vector according to the following equations:

$$\vec{R} = \frac{\vec{p}}{\sin(\theta)} \quad \vec{S} = \vec{q} + \frac{\vec{p}}{\tan(\theta)}$$

Returning to the example of FIG. 5, the cursor is positioned at the target position, which in this example is located at the center of the image. Therefore, the "rail" distance of "0.0" indicates that the rail should not move in order to keep the portion of the image selected by the user aligned with the target position. Similarly, the "slab" distance of "0.0" indicates that the slab also should not move in order to keep the portion of the image selected by the user aligned with the target position.

In the example of FIG. 6, the cursor is positioned at an off-center portion of the image. The apparatus 300 calculates the distance between the cursor and the target position in the <p,q> coordinate space, which corresponds to the <x,y> coordinate space. Using the equations provided above, the rail distance is calculated to be 111.6 mm, and the slab distance is calculated to be −136.9 mm. These distances indicate that if the carriage 142 is moved forward 111.6 mm along the rails 144 and the patient support 150 is moved backward 136.9 mm along the elevator frame 148, then the portion of the image selected by the user will be repositioned in line with the target position.

In some examples of the disclosure, in calculating the travel distances, the apparatus 300 may determine whether the patient support system 106 is capable of moving to the position selected by the user. For example, the rails 144 of the patient support system 106 may be of finite length and, therefore, may permit a carriage 142 mounted thereon only limited range of motion (e.g., until the end of the rails). In such an example, the user may select to align a position of the image with the isocenter, yet repositioning the patient in accordance with the user's selection may require the carriage 142 to move a distance longer than the distance between the current position of the carriage 142 and the end of the rails 144. In such a case, the computer 30 may compare these distances (which may be stored in the computer 30 prior to the comparison) and determine whether the user's selected position is in range or out of range, given the limited range of freedom that the carriage 142 may be moved along the rails 144. Similar travel restrictions and/or limits may apply to the movement of the patient support 150 along the elevator frame 148, or other repositionable components of the MRI magnet subsystem 100 in other examples of the disclosure.

In such an example in which the apparatus 300 determines that the user-selected position is in range, the apparatus 300 may continue with repositioning the patient support system 106. In such an example in which the user-selected position is determined to be out of range, the apparatus 300 may discontinue operations to reposition the patient support system 106. In some examples of the disclosure, the apparatus 300 may present an error message to the user (e.g., visual error message on the display 304, aural error signal, etc.).

In some examples, the above described in-range/out-of-range determination may be performed upon the user's selection of a target feature (e.g., the user clicking a button indicating that the cursor should be locked to the target feature). In other examples, the determination may be performed upon generation of the image such that each point of the image may be determined to be in range or out of range. In such an example, the apparatus 300 may be designed to visually indicate on the image the limits of the range of the patient handling system 106. Such a visual indication may be delivered to the user by means of a visual boundary (e.g., a line) separating the in-range portions of the image from the out-of-range portions. Such a visual indication may, in addition or alternatively, be delivered to the user by means of changing a color of the cursor, such that a first color may indicate that the cursor overlays an in-range portion of the image and a second color may indicate that the cursor overlays an out-of-range portion of the image.

In addition to the above described in-range/out-of-range determination, the apparatus 300 may execute other determinations in order to ensure proper operation of the MRI magnet subsystem 100, such as ensuring that the carriage 142 does not fall off the rails 144 or that the patient support 150 does not fall of the elevator frame 148. For example, the computer 30 may receive information indicating the current position of the rails 144 and/or elevator frame 148 from multiple sources and compare the positions to validate the information received. In one such example, information may be received from both an initialization file and from header information of the image file selected by the user. The information may then be compared to verify that the information appearing in the user selected image is consistent with the actual then-current status of the MRI magnet subsystem 100. In one example, the position and/or orientation of the patient handling system may be included in each file and compared to one another. In another example, patient identification information may be included in both files and compared to ensure that the image selected by the user is an image of the patient 154 currently occupying the MRI magnet subsystem 100. In other examples, the apparatus 300 may receive a timestamp from both files and compare the received timestamps to ensure that the image selected contains a current and up-to-date representation of the position and/or orientation of the patient support system 106. Upon validation of the information (e.g., verifying that the image file's header information substantially corresponds to the information included in the initialization file), the apparatus 300 may continue operations.

The apparatus 300 may instruct the patient support system 106 to reposition the patient 154 according to the calculated travel distances. In some examples of the disclosure, the calculated travel distances may be transmitted from the computer 30 to the MRI subsystem 10 in the form of instructions, instructing the mechanical and/or electrical components of the MRI subsystem 100 (e.g., actuators 103 and actuation control unit 105, for controlling the movement of rails 144 and elevator frame 148) how to reposition the MRI subsystem 100 such that the target anatomy of the patient 154 is properly aligned with the isocenter.

In one example, the computer 30 may transmit the calculated travel distances to the MRI subsystem 10 when the MRI subsystem 10 is turned on. In such an example, the MRI subsystem 10 may immediately respond to the instructions upon power up. In another example, the MRI subsystem may respond to the instructions upon activation of a switch, such as a user-activated rocker switch.

Figure 8:
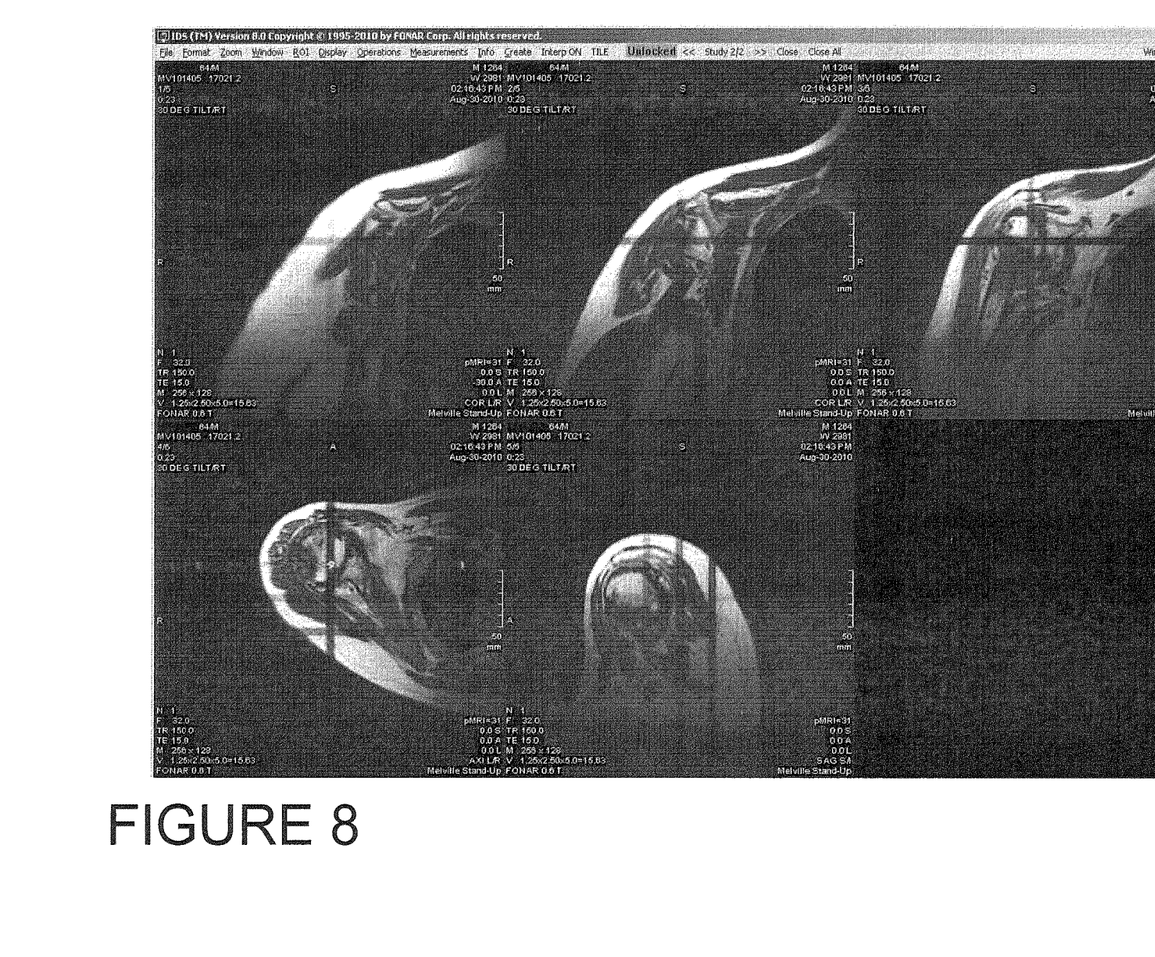
FIG. 8 is another example image displayed by the apparatus of FIG. 3 in accordance with an aspect of the disclosure.

FIG. 8 depicts a modified version of the image of FIG. 4 in which the shoulder of the patient 154 has been repositioned by the patient support system 106 according to the travel distance calculated by the apparatus 300. The isocenter is shown in the upper center image, which is a coronal cross-section at center of each of the superior, anterior, and left axes (as indicated by the "0.0 S, 0.0 A, 0.0 L" marking at the bottom right of the image). As compared to the image shown in FIG. 4, the isocenter in FIG. 8 is aligned with the head of the patient's humerus, and the views of the patient's shoulder are less blurred.

In some embodiments of the disclosure, the apparatus 300 may store information relating to the repositioned patient handing system 106, such as an updated position of the carriage 142 relative to the rails 144 and an updated position of the patient support 150 relative to the elevator frame 148. Storage of this information may be useful for future determinations of a then-current position of the patient handling system 106, for instance, to determine whether the patient handling system 106 is capable of being repositioned or whether such repositioning will cause the carriage 142 to fall off the rails 144 or cause the patient support 150 to fall off the elevator frame 148.

Figure 9:
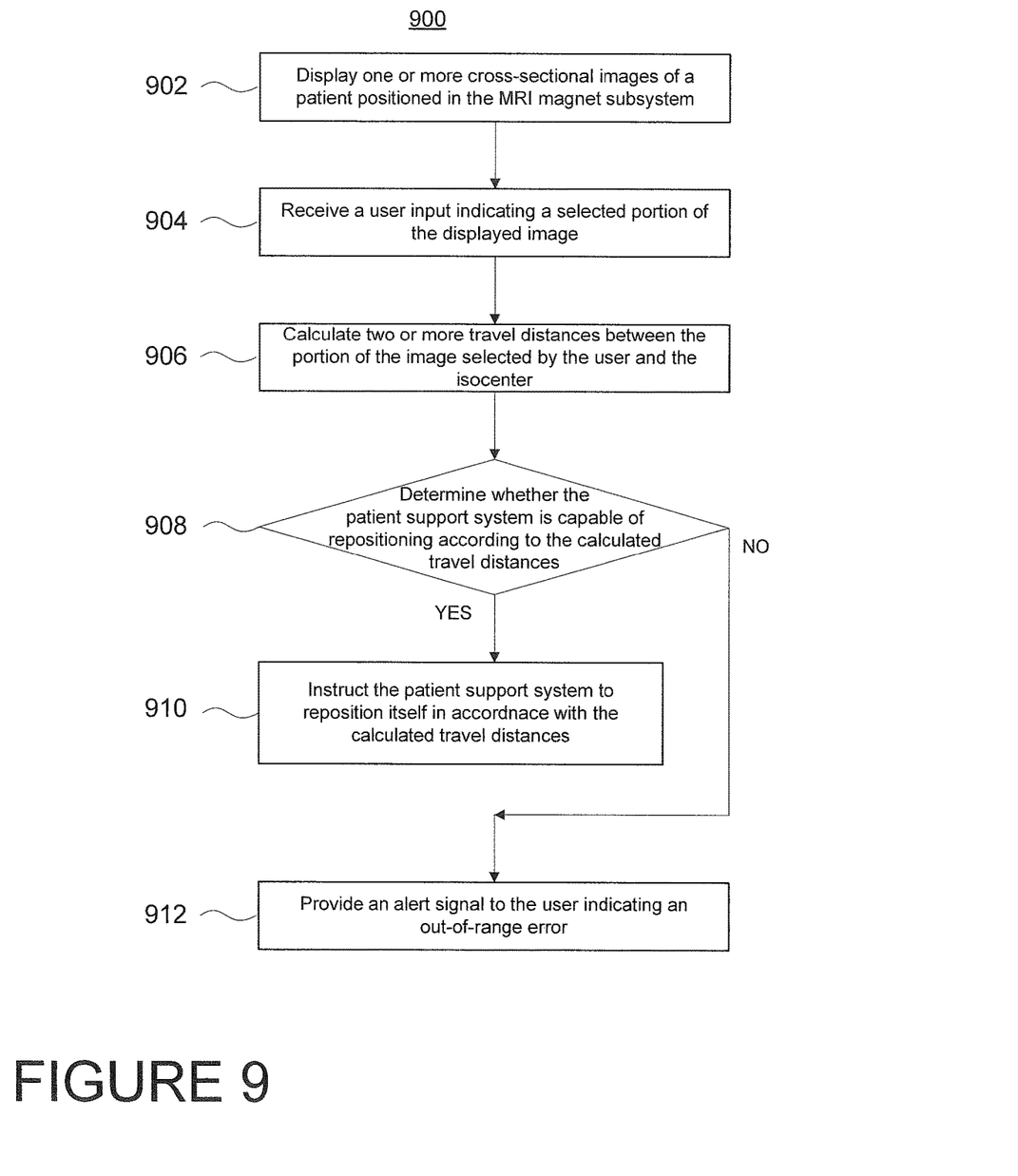
FIG. 9 is a flow diagram in accordance with an aspect of the disclosure.

FIG. 9 illustrates an example flow chart 800 in accordance with some of the aspects described above. In block 902, the apparatus 300 may display one or more cross-sectional images of a patient positioned in the MRI magnet subsystem. The apparatus 300 may receive a user input indicating a selected portion of the displayed image at block 904. For example, as described above, the user may select a feature of the patient's anatomy by moving a cursor over that feature, and the location of the cursor may be received by the apparatus 300. At block 906, the apparatus 300 may calculate two or more travel distances between the portion of the image selected by the user and the target position (e.g., isocenter). The calculated travel distances may indicate a distance that the patient support system 106 supporting the patient 154 in the MRI magnet subsystem 100 must reposition itself in order that the portion of the image selected by the user is aligned with the target position.

The apparatus 300 may determine whether the patient support system 106 is capable of repositioning according to the calculated travel distances at block 908. For example, as described above, the apparatus 300 may compare a travel distance to a current position of the patient handling system 106, and based on the comparison, determine whether repositioning the patient handling system 106 in accordance with the travel distances may cause the bed supporting the patient 154 to fall off its support. If the apparatus 300 determines that the patient support system 106 is capable of repositioning according to the calculated travel distances, operations may continue at block 910, in which the apparatus 300 may instruct the patient support system 106 to reposition itself in accordance with the calculated travel distances. If the apparatus 300 determines that the patient support system 106 is not capable of repositioning according to the calculated travel distances, operations may continue at block 912, in which the apparatus 300 may provide an alert signal to the user indicating an out-of-range error (e.g., an error signal indicating that portion of the image selected by the user cannot be aligned with the isocenter of the MRI imaging subsystem 100 given the patient handling system's 106 limited range of movement).

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of aligning a patient positioned on an inclined bed with a target position of a magnetic resonance imaging system, the method comprising:
displaying one or more cross-sectional images of the patient, at least one of the cross-sectional images featuring an anatomical feature of interest of the patient, said one of the cross-sectional images forming a plane having first and second axes in a first coordinate space, the first coordinate space further comprising a third axis orthogonal to the plane of said cross-sectional image;
receiving, at a computer, a positional input corresponding to a location of the anatomical feature of interest in the first coordinate space of said cross-sectional image;
receiving, at the computer, an angular input indicating a degree of incline of the bed on which the patient is positioned, wherein the bed is capable of being translated along a plurality of axes including a first and second axes of a second coordinate space, said first and second axes of the second coordinate space comprising a lengthwise direction of the inclined bed and a lengthwise direction of the bed in an uninclined state;
determining, at the computer, a distance between the location of the anatomical feature of interest and the target position of the magnetic resonance imaging system along each of the first and second axes of the first coordinate space based on the input corresponding to the location of the anatomical feature of interest in the cross-sectional image;
calculating, at the computer, a coordinate transformation of the determined distance from the first coordinate space to the second coordinate space based on the angular input, wherein the calculation converts the determined distance into first and second travel distances along the first and second axes of the second coordinate space, respectively; and
repositioning the inclined bed within the magnetic resonance imaging system according to both the first travel distance and the second travel distance.

2. The method of claim 1, wherein the first axis of the second coordinate space corresponds to a degree of freedom of the magnetic resonance imaging system along which a carriage supporting the inclined bed is capable of moving.

3. The method of claim 2, wherein the second axis of the second coordinate space corresponds to a degree of freedom of the magnetic resonance imaging system along which the inclined bed is capable of moving independent of the carriage.

4. The method of claim 1, further comprising:
calculating first and second maximum ranges along each of the first and second axes of the second coordinate space, respectively;
comparing the first maximum range to the first travel distance;
comparing the second maximum range to the second travel distance;
if neither of the travel distances exceeds the corresponding maximum range, repositioning the inclined bed within the magnetic resonance imaging system according to both the first travel distance and the second travel distance.

5. The method of claim 4, further comprising:
if either of the travel distances exceeds the corresponding maximum range, providing a signal to a user indicating an out-of-range error.

6. The method of claim 5, wherein the out-of-range error further comprises an indication as to which of the first travel distance and the second travel distance exceeds the corresponding maximum range.

7. The method of claim 1, wherein the target position is the isocenter of the magnetic resonance imaging system.

8. The method of claim 7, wherein the isocenter includes any point within a 0.1 mm radius of a centerpoint of a magnet included in the magnetic resonance imaging system.

9. The method of claim 7, wherein the isocenter includes any point within a 2.0 cm radius of a centerpoint of a magnet included in the magnetic resonance imaging system.

10. A device for aligning a patient positioned on an inclined bed of a patient handling system with a target position of a magnetic resonance imaging system, the device comprising:
- a memory storing information pertaining to a current position and tilt of the patient handling system within the magnetic resonance imaging system; and
- a processor coupled to the memory, the processor configured to:
  - display one or more cross-sectional images of the patient within the magnetic resonance imaging system, at least one of the cross-sectional images featuring a target anatomical feature of the patient, said one of the cross-sectional image forming a plane having first and second axes in a first coordinate space, the first coordinate space further comprising a third axis orthogonal to the plane of said cross-sectional image;
  - receive an input corresponding to a location of the target anatomical feature in the first coordinate space of said cross-sectional image;
  - determine a distance between the location of the target anatomical feature and the isocenter of the magnetic resonance imaging system along each of the first and second axes of the first coordinate space based on the input;
  - calculate a coordinate transformation of the determined distance from the first coordinate space to a second coordinate space based on the current tilt information, wherein the bed is capable of being translated along a plurality of axes including a first and second axes, wherein the calculation converts the determined distance into first and second travel distances along the first and second axes of the second coordinate space, respectively; and
  - reposition the target anatomical feature, according to both the first travel distance and the second travel distance, to the isocenter.

11. The device of claim 10, wherein the second axis of the second coordinate space corresponds to a degree of freedom along which a component of the patient handling system is capable of translating parallel to one of an anterior, superior, or left axis of the patient.

12. The device of claim 11, wherein the first axis of the second coordinate space corresponds to a degree of freedom along which a component of the patient handling system is capable of linearly moving relative to at least one rail.

13. The device of claim 11, wherein the second axis of the second coordinate space corresponds to a degree of freedom along which a component of the patient handling system is capable of linearly moving relative to at least one slab.

14. The device of claim 10, wherein the first axis and the second axis of the second coordinate space are not perpendicular.

15. The device of claim 10, wherein the processor is further configured to:
- receive information indicating a current position of the patient handling system from a first file;
- receive information indicating a current position of the patient handling system from a second file, the second file including the cross-sectional images of the patient displayed by the processor;
- compare the received information of the first file to the received information of the second file; and
- only if the received information of the first file substantially corresponds to the received information of the second file, reposition the patient within the magnetic resonance imaging system according to both the first travel distance and the second travel distance.

16. The device of claim 10, wherein the isocenter of the magnetic resonance imaging system includes any point within a 0.1 mm radius of a centerpoint of a magnet included in the magnetic resonance imaging system.

17. The device of claim 10, wherein the isocenter of the magnetic resonance imaging system includes any point within a 1.0 mm radius of a centerpoint of a magnet included in the magnetic resonance imaging system.

18. The device of claim 10, wherein the isocenter of the magnetic resonance imaging system includes any point within a 2.0 cm radius of a centerpoint in the magnetic resonance imaging system at which the magnetic field and the transmitted radio frequency field are substantially uniform.

19. The method of claim 1, wherein said one of the cross-sectional images is captured at a plane that is antiparallel to any plane formed by any two axes of the plurality of axes along which the inclined bed is capable of translating.

20. The device of claim 10, wherein said one of the cross-sectional images is captured at a plane that is antiparallel to any plane formed by any two axes of the plurality of axes along which the patient handling system is capable of translating.

21. The method of claim 1, wherein said one of the cross-sectional images is captured at a plane that is parallel to the first and second axes of the second coordinate space.

22. The device of claim 10, wherein said one of the cross-sectional images is captured at a plane that is parallel to the first and second axes of the second coordinate space.

* * * * *